(12) United States Patent
Benz et al.

(10) Patent No.: US 11,285,296 B1
(45) Date of Patent: Mar. 29, 2022

(54) APPARATUS FOR A NON-INVASIVE INTERVENTIONAL SHEATH SECUREMENT DEVICE

(71) Applicant: Philip Benz, Milwaukie, OR (US)

(72) Inventors: Philip Benz, Portland, OR (US); Patrick Scranton, Vancouver, WA (US)

(*) Notice: Subject to any disclaimer, the term of this patent is extended or adjusted under 35 U.S.C. 154(b) by 0 days.

(21) Appl. No.: 17/464,079

(22) Filed: Sep. 1, 2021

Related U.S. Application Data

(60) Provisional application No. 63/148,336, filed on Feb. 11, 2021.

(51) Int. Cl.
*A61M 5/178* (2006.01)
*A61M 25/02* (2006.01)
*A61M 25/06* (2006.01)

(52) U.S. Cl.
CPC ........ *A61M 25/02* (2013.01); *A61M 25/0662* (2013.01); *A61M 2025/024* (2013.01); *A61M 2025/0266* (2013.01); *A61M 2025/0681* (2013.01)

(58) Field of Classification Search
CPC .......... A61M 25/02; A61M 2025/0213; A61M 2025/024; A61M 2025/0266; A61M 2025/028; A61M 2025/0293
See application file for complete search history.

(56) References Cited

U.S. PATENT DOCUMENTS

| | | | |
|---|---|---|---|
| 8,162,898 B1 | 4/2012 | Wright | |
| 8,197,447 B2 | 6/2012 | Wright | |
| 10,092,729 B2 | 10/2018 | Beran | |
| 2006/0270994 A1* | 11/2006 | Bierman | A61M 25/02 604/180 |
| 2012/0041377 A1* | 2/2012 | Haak | A61M 25/02 604/180 |
| 2015/0367102 A1* | 12/2015 | Andino | A61M 25/02 604/179 |

* cited by examiner

*Primary Examiner* — Rebecca E Eisenberg

(57) ABSTRACT

A non-invasive interventional sheath securement device is used by clinicians for removably securing a sidearm of a vascular access sheath for the purpose of preventing the sheath's movement through or out of a puncture site during its deployment in an interventional medical procedure.

15 Claims, 9 Drawing Sheets

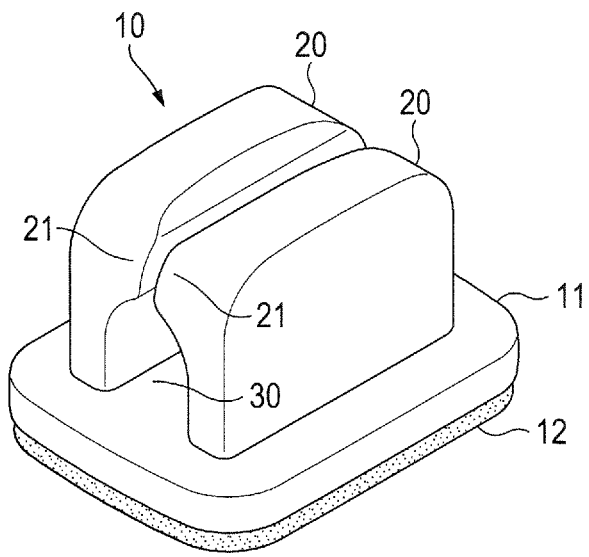
FIG. 1a
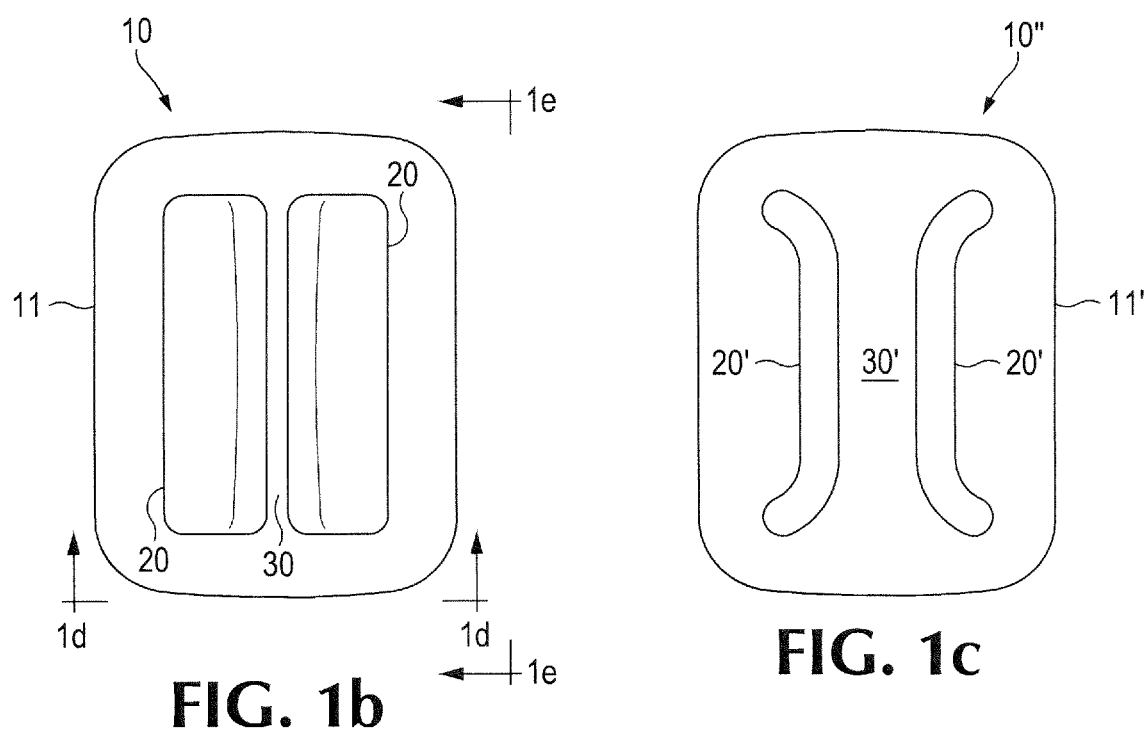
FIG. 1b  FIG. 1c

APPARATUS FOR A NON-INVASIVE INTERVENTIONAL SHEATH SECUREMENT DEVICE

This Non-Provisional Application contains matter included in Provisional Applications No. 63/122,223 filed on Dec. 7, 2020, and No. 63/148,336 filed on Feb. 11, 2021 by Philip Benz.

FIELD OF THE INVENTION

The invention relates generally to the field of interventional medicine. More particularly, the invention relates to a device that a clinician would use to prevent a vascular access sheath from slipping inside a puncture site during an interventional medical procedure.

BACKGROUND OF THE INVENTION

This invention relates particularly to vascular access sheaths, used during interventional medical procedures, through which catheters, guidewires, stent delivery systems, etc. are inserted into a patient's vasculature, i.e. blood vessels. The use of these sheaths is well-known and examples of the fields of medicine commonly using them include cardiac catheterizations, interventional radiology, and vascular surgery and interventions.

Prior to inserting any guidewires or catheters or other equipment into a patient's vascular system, an access sheath is inserted percutaneously into a puncture site that is made in a blood vessel, e.g. a radial or femoral artery or a femoral vein. The sheath includes a hub located on the end opposite the end of the cannula, which has a lumen, that is inserted into the blood vessel. The hub further includes a hole located on the end opposite the cannula, and a hemostatic valve inside the hole, which serves to keep blood from the blood vessel from escaping out of the sheath. The hub also connects to a sidearm with a stopcock that enables the operator to take a sample of blood when needed. The sheath remains in place for the duration of the procedure, unless it is replaced by another sheath or a sheathless catheter having different characteristics, e.g. a different inside diameter of its cannula.

The hub is made of a rigid material. The hemostatic valve inside the hub is made of a flexible elastomeric material. The cannula portion of the sheath (which is inserted into the blood vessel) is a thin-walled plastic tube. The sidearm, attached to the hub, is a tube made of a flexible, compressible plastic material that is usually transparent and has a lumen running its entire length and is never inserted into a blood vessel. The stopcock on the sidearm is made of rigid plastic materials.

When a guidewire or catheter must be inserted into the blood vessel, the operator pushes it through the hole in the hub and past the hemostatic valve into the blood vessel, where it is manipulated to achieve the goals of that interventional medical procedure, whether diagnostic or therapeutic. Generally, several guidewires and catheters are passed in and out of a sheath during course of such procedure. The sidearm is generally used occasionally to take samples of blood, or to remove blood from the interior of the sheath to help avoid thrombosis or distal embolization prior to removing the sheath at the end of the procedure.

During the course of an interventional procedure, the area around the puncture site is commonly bloody, as a result of blood leaking through the hemostatic valve in the hub and from oozing from the puncture site, in particular when equipment, e.g. guidewires and catheters, being passed through the sheath is exchanged. Generally, as procedure length and number of equipment exchanges increases, so does the amount of blood around the puncture site. Blood often is concentrated in the area immediately surrounding the puncture site, though some blood can spread or splash onto the sterile drape that surrounds the puncture site.

Sheaths, particularly for use in the radial artery, have a lubricious. i.e. slippery coating that facilitates insertion and removal of the sheath while reducing disturbance or trauma to the tissue surrounding the puncture site. While this coating affords the potential benefits of improved patient comfort, reduced tissue damage, and reduced opportunity for puncture site complications, it also creates opportunity for accidental sheath dislodgement, particularly when exchanging equipment that is passed through the sheath. The motion of moving guidewires and catheters in and out of the sheath, due to the hemostatic valve and the inside walls of the sheath, in contact with said wires and catheters, often has the effect of moving the sheath in and out of the puncture site, with the risk that complete removal would result in uncontrolled bleeding. Thus, there is a need for securing the sheath in place during the course of an interventional procedure, without obstructing access to the hub or the sidearm, and while enabling convenient sheath removal at the end of the procedure.

Existing partial solutions to this need include several products that are described in Cath Lab Digest articles: i) "How Do You Secure Your Radial Sheath?" in its January, 2018 issue (volume 26, issue 1); ii) "Securing the Radial Sheath" in its November, 2020 issue (volume 28, issue 11). All but one of the products and techniques used involve placement of adhesive-backed devices under, around, or over the sheath at its insertion point in the puncture site. Some operators place folded up gauze under the hub immediately distal to the puncture site, with a clear adhesive patch (e.g. Tegaderm) placed over the sheath and gauze with only the end of the hub exposed. Other operators use a similar technique but without use of the gauze. Devices adapted to or at least indirectly designed for addressing this problem include: an adhesive SorbaView bandage, either by itself or in conjunction with a larger adhesive placed over it and the sheath; a StatLock which is adhesively attached to a patient's wrist area or the drape, and requires tying strings to secure the sheath; a StatLock™ which is adhesively attached to the wrist or drape and uses a rigid plastic fastener to fasten the sheath in place: a StayFix adhesive tape; a Dale Hold-n-Place adhesive bandage that adheres to the patient's wrist immediately distal to the puncture site and has adhesive 'arms' that attach to the sheath, which can be used with or without an additional adhesive patch. All of these techniques require the adhesive to be placed over or at least in very close contact with the area around the puncture site. Another technique described in the article involved using a metal hemostat (scissors-type clamp) to secure the sidearm to a towel near or a drape surrounding the puncture site.

StatLock™ IV stabilization devices are marketed by the BD company (www.bd.com) for the purpose of stabilizing PICC lines, and intravenous and intra-arterial catheters, most of which are individually specific to certain models and brands of catheter. Their intended use does not include arterial interventional sheath stabilization. Examples of StatLock device securement mechanisms include: a plastic retainer attached to adhesive strips that is placed over the connector of a catheter; hinged post and door design mechanism mounted on an adhesive strip; snap-cap retention mating to hubs of catheters; a hinged retainer attached to an adhesive strip that snaps in place over the catheter; strands, attached to adhesive, that wrap around a catheter. Many of these securement mechanisms require mating features on the target cannula in order to function. None of the StatLock products are for use or can be used with an interventional sheath sidearm. Some clinical users have attempted to use StatLock devices to stabilize an interventional sheath by placing it directly over the sheath during its deployment with, as shown in the Cath Lab Digest articles cited above, limited usability.

Additional prior art, though only tangentially related, is present in the following patents: U.S. Pat. No. 8,162,898 by Wright; U.S. Pat. No. 8,197,447 by Wright; and, U.S. Pat. No. 10,092,729 by Beran.

Wright, in '898, describes a venipuncture base plate, which is adhesively attached to a patient's skin either distally or proximally to an intravenous venipuncture site. It is also attached to a catheter by means of a catheter fitting into which it is inserted, this catheter fitting element then being attached onto the venipuncture base place by snapping into a rigid receiver mounted on top of the adhesive material. This device is designed for securing intravenous catheters, which are generally more stable than interventional access sheaths since they are not subject to equipment moving in and out of them and thus less likely to have blood on the adjacent skin.

Wright, in '447, describes a venipuncture site protector that includes a rigid hollow cover mounted on adhesive material that is attached to the patient similarly to '898. An IV catheter passes into the cover through a slot located in the proximal end, with the venipuncture site located in an opening in the adhesive material and under the cover. The shell is sized so as to retain the IV catheter in place. Similarly to '898, this device is designed for securing intravenous catheters, which are generally more stable than interventional access sheaths since they are not subject to equipment moving in and out of them and thus less likely to have blood on the adjacent skin.

Beran, in '729, describes a catheter securement device that is adhesively attached to a patient's skin similarly to '898, and that has pivoting members that work to secure the catheter in place. Also similarly to '898, this device is designed for securing intravenous catheters, which are generally more stable than interventional access sheaths since they are not subject to equipment moving in and out of them and thus less likely to have blood on the adjacent skin.

Problems experienced with using the techniques requiring adhesives placed adjacent to or over the sheath at its insertion point in the puncture site include: inconvenient deployment onto the patient; once blood or any other fluid infiltrates onto the adhesive layer attached to the skin, the adhesiveness degrades: "it is a mess and stops working" (Cath Lab Digest, "How Do You Secure Your Radial Sheath", vol 26, issue 1, January 2018). Any devices incorporating adhesive attachment to the area immediately surrounding the puncture site may be compromised when blood begins to accumulate in said area. Further, removing adhesive immediately adjacent the puncture site following end of the procedure risks dislodgement of the sheath and potential trauma to the puncture site area.

The technique in which a hemostat is used to secure the sidearm to a towel near the puncture site area avoids the use of adhesives adjacent the puncture site area but requires that a towel be placed near the area. This is not generally done unless significant bleeding is present so represents an additional item and step in order to secure the access sheath. Further it is inconvenient to use in this respect and can constrict or possibly damage the sidearm, which would result in limiting or entirely obstructing the ability to draw blood from it when needed.

Obstructing access to the hub of the sheath must be prevented during the procedure, thus any device must not present an obstacle to the end of the sheath hub. In addition, sheaths are often changed out, e.g. substituting a larger sheath in the middle of a procedure and devices must not prevent fast sheath substitutions. In no event can the cannula of the sheath be constricted or kinked.

Thus, there is a need for a convenient, easily deployable and removable means of properly securing a vascular access sheath in a puncture site in a blood vessel, in particular in a radial artery, to avoid its dislodgement, for the duration of an interventional medical procedure.

The Non-Invasive Interventional Sheath Securement Device of the present invention addresses this need as described in the embodiments included herein. Comprised of a base on the top surface of which is located at least a sheath sidearm retention channel, the sheath securement device is adhered to a patient's body surface, or the surface of a sterile drape, that is in proximity to but not necessarily immediately adjacent to the puncture site in which the sheath is placed during an interventional procedure, in order to avoid excessive exposure to blood from said puncture site. The interventional sheath sidearm is pressed by the clinician into the retention channel to prevent slippage of the sheath in and out of the puncture site for the duration of the procedure, particularly when equipment like catheters or guidewires are passed in and out of the sheath. At the end of the procedure, the clinician pulls the sidearm from the retention channel, then removes the securement device when the drape is removed, generally prior to removing the sheath from the puncture site. The sidearm must be able to be easily and repeatedly removed and inserted into the device to permit passage of fluids, e.g. blood, therethrough when needed and any securement device must not damage it.

The sheath sidearm retention channel of the securement device is for the purpose of removably capturing an interventional sheath sidearm during said sheath's deployment, the channel having a width, which may be constant or may vary from one end to the other, and may further be formed from facing sheath sidearm retention tabs, one or more of which may further include a sheath sidearm retention bead on an inside surface of said tabs.

At least one sheath sidearm retention bead may be present along all or part of the length of one or more sides at the top end of a retention channel or one or more retention tabs, for the purpose of restricting upward movement of the sidearm during insertion into the channel.

The width of the channel may be constant across its length, or it may vary, for example the width near the center may be shorter than the width at one or both ends. The channel may alternatively be embedded in the base of the device, thus retention tabs may be absent from said base.

An adhesive or mechanical clamping features attach the securement device to the patient, drape or towel near the puncture site.

The securement device may also be seen to include a securement device base and at least one pair of sidearm retention tabs that face each other to form the sidearm retention channel for the purpose of removably capturing an interventional sheath sidearm.

BRIEF DESCRIPTION OF THE DRAWINGS

FIG. 1a is a perspective view of an embodiment of the non-invasive interventional sheath securement device of the present invention.

FIG. 1b is a top view of the embodiment of the sheath securement device shown in FIG. 1a.

FIG. 1c is a top view of the securement device shown in FIG. 1a, but with a different embodiment of the tabs.

FIG. 1d is an end view of the device shown in FIG. 1a.

FIG. 1e is a side view of the device shown in FIG. 1a.

FIG. 1g is an alternative embodiment of the device shown in FIG. 1a.

FIG. 2b is an end view of the device taken along lines 2b-2b of FIG. 2a.

FIG. 2c is a side view of the device taken along lines 2c-2c of FIG. 2a.

FIG. 2d is a top perspective view of the device shown in FIG. 2a.

DETAILED DESCRIPTION OF THE PREFERRED EMBODIMENTS

Figure 1D:
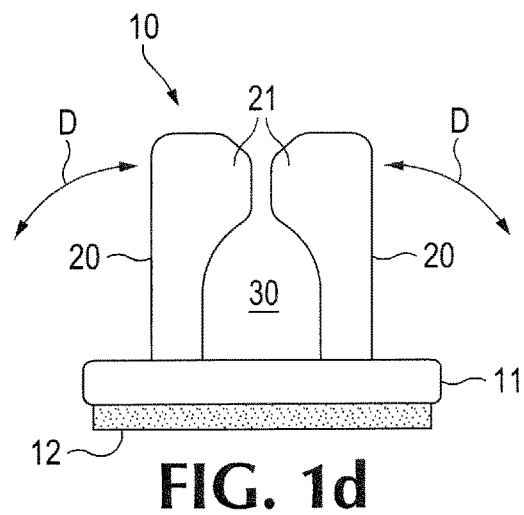

The perspective view of FIG. 1a shows the non-invasive interventional sheath securement device 10 having a securement device base 11 to which is attached an adhesive material 12 on its bottom side for the purpose of adhering said device 10 to the surface onto which it is deployed. The top side of base 11 includes at least two sheath sidearm retention tabs 20, in this embodiment positioned generally parallel with each other to form a sheath sidearm retention channel 30 between them that is for the purpose of removably capturing an interventional sheath sidearm during said sheath's deployment in a medical procedure. Formed onto the inside surfaces near the retention tabs' 20 top edges is a hook feature or retention bead 21 that narrows the distance between the tabs' 20 inside surfaces at their top edges while providing a larger space comprising the retention channel 30 underneath, the beads 21 serving as an obstacle to the sidearm's 112 (not shown in this Figure) removal in the upward direction from the channel 30. Although FIG. 1 shows the tabs 20 as generally having the same height and length, they may alternatively have different heights and lengths. The beads 21 are shown to have bevels on their top inside and bottom inside edges to facilitate insertion and removal of tubes, in particular sidearms 112 of interventional vascular access sheaths 110 (not shown in this Figure).

The top view of FIG. 1b shows the sheath securement device 10 having a device base 11 on the top side of which are located at least two sidearm retention tabs 20 between which is formed a sidearm retention channel 30.

The top view of FIG. 1c shows a non-invasive interventional sheath securement device 10" that has two sheath sidearm retention tabs 20', which form a sheath sidearm retention channel 30' between them, all of which are located on the top side of a securement device base 11'. The tabs 20' have a short section on their ends angled outward towards the perimeter of the base 11'.

The end view of FIG. 1d shows sheath securement device 10 having two retention tabs 20, each of which has a sheath sidearm retention bead 21, as a kind of projecting rim running along the inside surface of the top edge of each tab 20. The area under the retention beads 21 forms a sidearm retention channel 30 that runs along the length of the tabs 20. The retention channel 30 and tabs 20 are located on the top side of the base 11, on the bottom side of which is located an adhesive material 12. The adhesive 12 would adhere to the bottom surface of the base 11, and also adhere to the surface on which the device 10 is deployed, thus adhesive is present on both sides of the material 12. The tabs 20, when formed with a construction, or of a semi-rigid or flexible material, which permits flexing, are able to deflect laterally, generally in the directions D, more particularly a direction D away from the facing retention tab 20, when objects pass between the beads 21, which are shown to have a chamfer or bevel on their top and bottom sides to facilitate insertion and removal of said objects. The maximum width of the retention channel 30 is generally less than or equal to the maximum outside diameter of a sheath sidearm 112 (not shown in this FIG. 1d). Alternative embodiments of the device 10 may have tabs 20 of unequal height or length, and a width or diameter of the retention channel 30 that varies along its length.

Figure 1E:
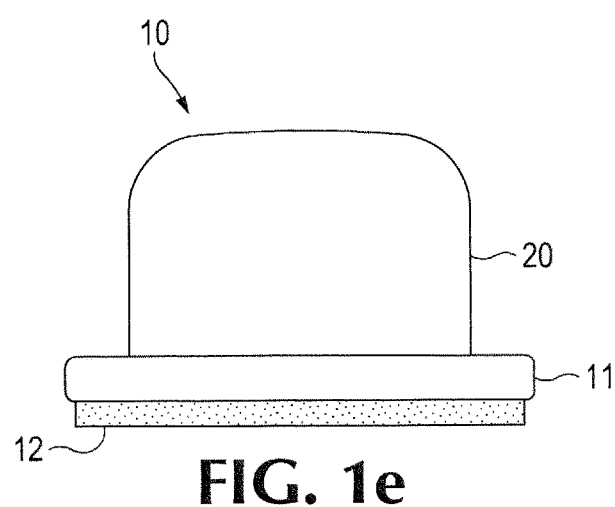

The side view of FIG. 1e shows the securement device 10 having at least two sidearm retention tabs 20 (only one of which is shown in this view) located on the top side of the securement device base 11, on the bottom side of which is located adhesive material 12.

Figure 1F:
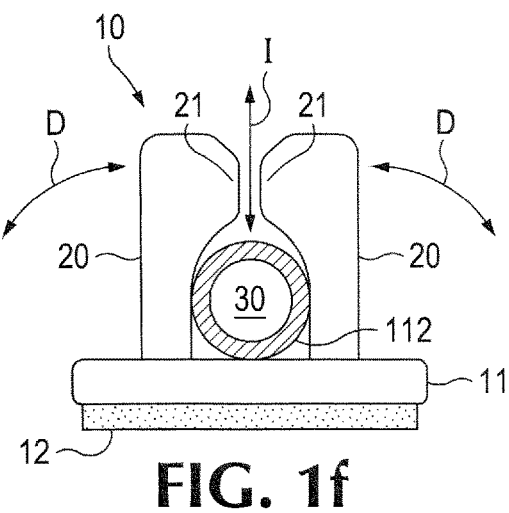
FIG. 1f is an end view of the device shown in FIG. 1d, with a sheath sidearm inserted.

The end view of the sidearm retention channel 30 of the securement device 10 is shown in FIG. 1f with a sidearm 112, in partial section view, inserted into it, between the interior surfaces of the retention tabs 20 and under the bottom edges of the retention beads 21, i.e. in said retention channel 30. An embodiment may have shorter tabs 20 so that the top surface of the sidearm 112 is in contact with the bottom surfaces of beads 21. The tabs 20 and channel 30 are located on the top side of base 11, on the bottom side of which is located adhesive material 12. The tabs 20 are shown to be able to deflect at least laterally when made of a generally flexible or semi-rigid material, generally and to varying extent in directions D, when objects, i.e. a sidearm 112, are pressed down in the vertical axis I, through the space between the beads 21 that are opposite each other, and into the channel 30. The tabs 20 may flex along their entire height, or only at a certain point or points along their height, in particular in the area where they connect to the base 11.

Figure 1G:
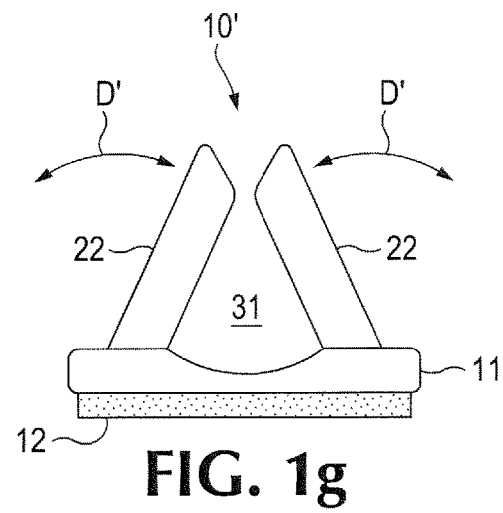

FIG. 1g shows an alternative embodiment of sidearm retention tabs 20 as sheath sidearm retention tabs 22 of the non-invasive interventional sheath securement device 10', where they are inclined at an inward angle with their top edges closer than their bottom edges that are attached to the base 11. The tabs 22 are shown to be able to deflect laterally, generally in the directions D' when objects pass between their top edges, which are shown to have a chamfer or bevel on their top sides to facilitate insertion of said objects. An embedded sheath sidearm retention channel 31 is thus formed in a generally triangular shape (in its cross-section) and further has a partially concave bottom surface between tabs 22. Said embedded sheath sidearm retention channel 31 may also be present on a base 11 without any tabs 22 and having a deeper concave shape in the base 11 to accommodate the sidearm 112 (not shown in this FIG. 1g). In this embodiment, the embedded retention channel 31 would have a generally circular cross section that is truncated at the top and have an open top side and open ends, and may also have a sidearm retention bead 21 placed along part or all of the edge on the top side opening of the embedded retention channel 31. An adhesive material 12 is attached to the bottom side of base 11.

Figure 2A:
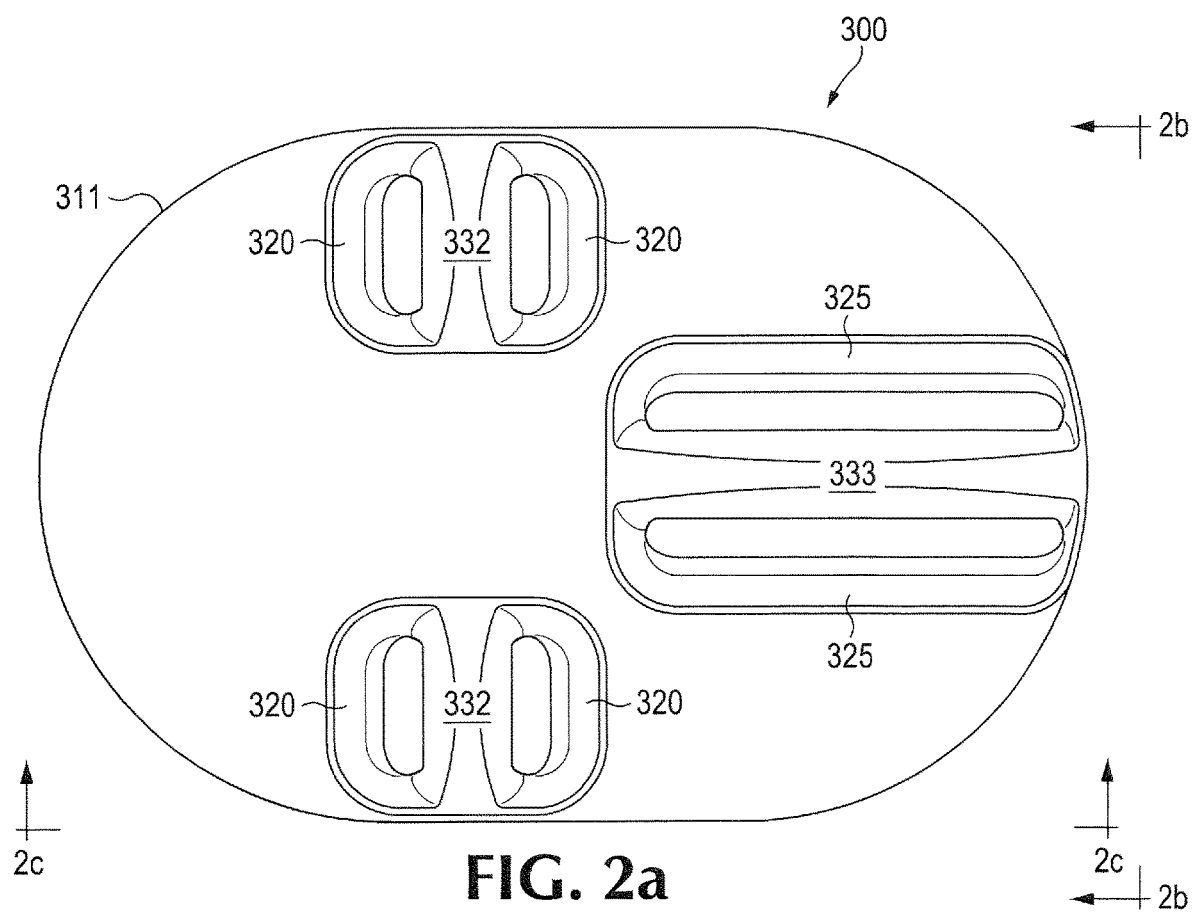
FIG. 2a is a top view of the frame of a preferred embodiment of the non-invasive interventional sheath securement device of the present invention.

The top view of FIG. 2a shows a preferred embodiment of the non-invasive interventional sheath securement device 300 of the present invention. On the top surface of the securement device base 311 are located: i) two pairs of short sheath sidearm retention tabs 320, each pair forming a short sheath sidearm retention channel 332 between their interior sides; and ii) one pair of long sheath sidearm retention tabs 325 that form a long sheath sidearm retention channel 333 between their interior sides. The sidearm retention channels 332 and 333 each have interior widths that vary from one end to the other, and are for the purpose of removably capturing an interventional sheath sidearm during said sheath's deployment in a medical procedure.

Figure 2B:
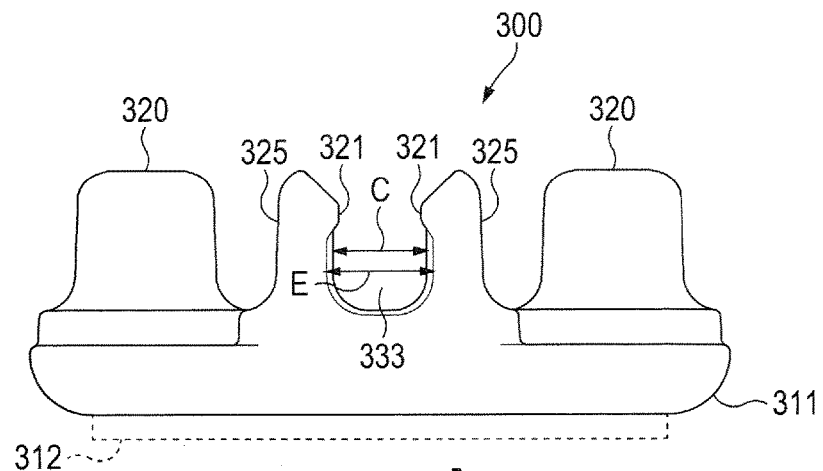

The end view of FIG. 2b, taken along lines 2b-2b of FIG. 2a, shows the device 300 having a long retention channel 333 formed by the long retention tabs 325, the top sections of which each include sheath sidearm retention beads 321 on the retention tabs' 325 inside surfaces that face each other. The retention beads 321 serve as an obstacle to the sidearm's 112 (not shown in this Figure) removal in the upward direction from the channel 333. Placed on the top side of the base 311 and perpendicularly to the long retention tabs 325 are the short retention tabs 320. Adhesive material 312, for the purpose of adhering the device 300 to the patient, is shown in phantom attached on the bottom surface of the base 311. The adhesive 312, in this embodiment, adheres to the bottom surface of the base 311, and also to the surface onto which the device 300 is deployed, thus adhesive is present on both sides of the material 312. The long retention channel 333 has a width that varies along its length, in this embodiment forming an internally tapered sheath sidearm retention channel that has a width C located in the center of the channel 333, having a shorter dimension than width E located at one or more ends of the channel 333.

Figure 2C:
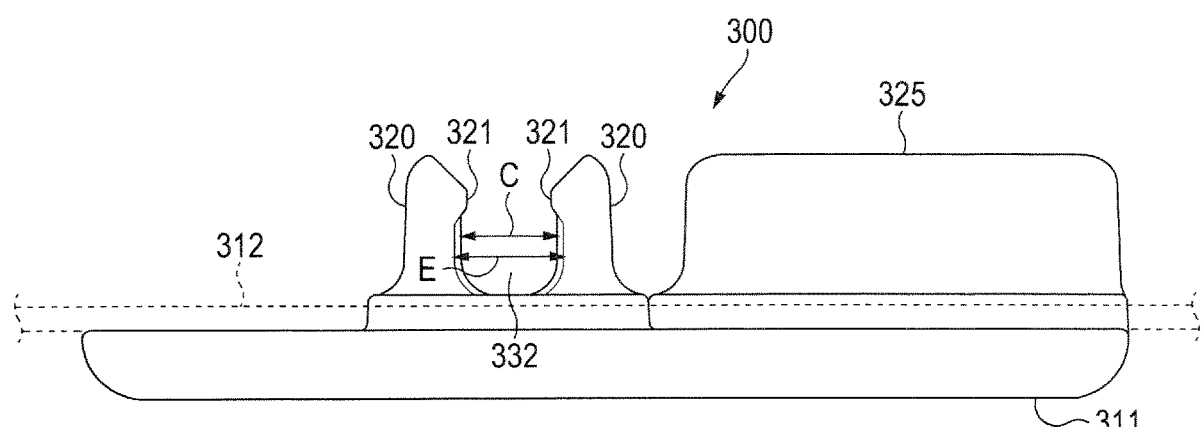

The side view of FIG. 2c, taken along lines 2c-2c of FIG. 2a, shows the device 300 having at least one short retention channel 332 formed by at least two short retention tabs 320, each of which has a retention bead 321 on the tabs' 320 inside surfaces that face each other. The beads 321 serve as an obstacle to the sidearm's 112 (not shown in this Figure) removal in the upward direction from the channel 332. Placed on the top side of the base 311 and perpendicularly to the short retention tabs 320 are the long retention tabs 325. Adhesive material 312, for the purpose of adhering the device 300 to the patient, is shown in phantom on the top surface of the base 311, the edges of said adhesive 312 extending beyond the perimeter edge of the base 311. Adhesive is present on only the bottom side of the material 312, where it fastens to the top surface of the base 311 and where the material extending beyond the perimeter of the base 311 adheres to the surface onto which device 300 is deployed. The at least one short channel 332 has a width that varies along its length, in this embodiment forming an internally tapered sheath sidearm retention channel, i.e. a channel that has an internally tapered width, which has a width C located in the center of the channel 332, having a shorter dimension than width E located at one or more ends of the channel 332.

Figure 2D:
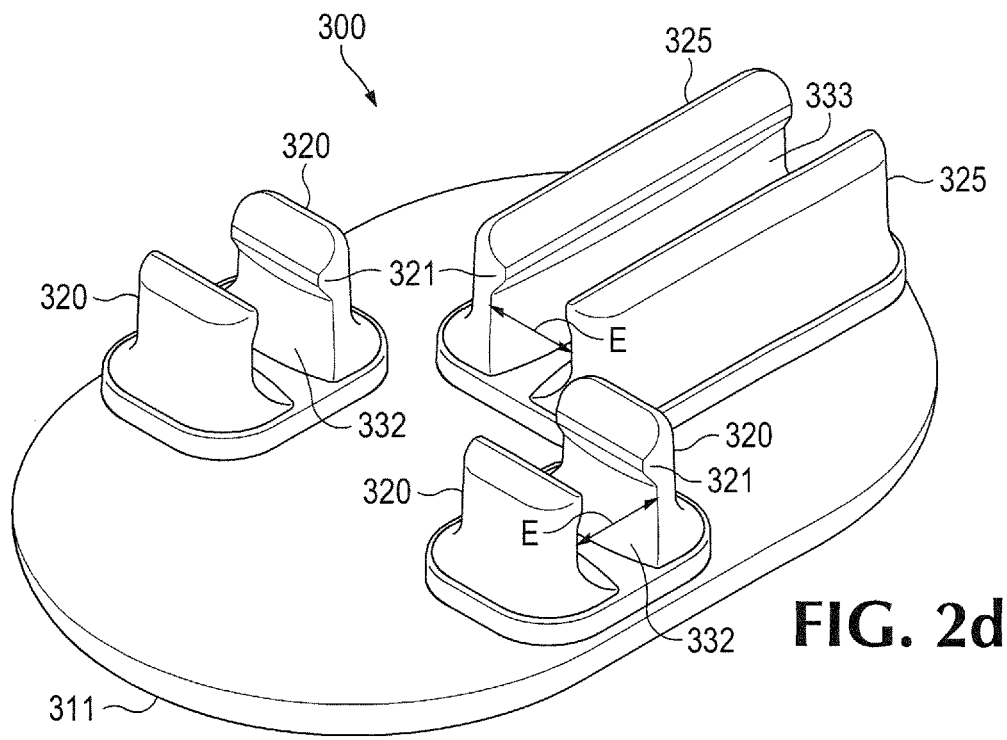

The top perspective view of FIG. 2d shows the following elements placed on the top surface of the base 311 of the device 300: i) two pairs of short retention tabs 320 that each form between them a short retention channel 332, the tabs 320 each including a retention bead 321 on the inside surface of their top portion; ii) end width E is shown for one of the short channels 332; iii) one pair of long retention tabs 325 that form between them a long retention channel 333, the tabs 325 each including a retention bead 321 on the inside surface of their top portion; iv) end width E is shown for the long channel 333. As shown, the internal taper of the channels 332 and 333 is formed by convex inside walls of the sidearm retention tabs 320 and 325, i.e. the inside walls of the sidearm retention tabs 320 and 325 that face the center of such channels 332 and 333 are convex in shape, thus more particularly forming convex internally tapered channels 332 and 333.

Figure 2E:
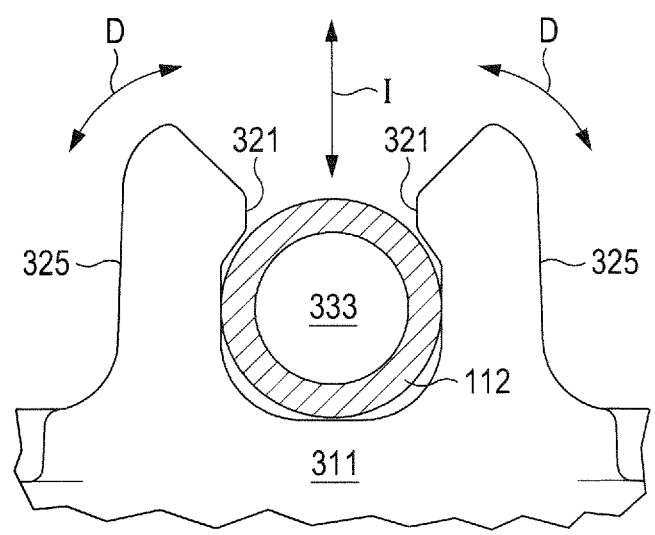
FIG. 2e is an end view, with parts removed for clarity, of the device shown in FIG. 2b.

The end view of FIG. 2e shows the long retention channel 333, formed between long tabs 325 placed on the top of the base 311, each of which includes a retention bead 321 on the inside surface of its top portion. A sheath sidearm 112 is shown to be removably inserted in direction I into the channel 333, the tabs 325 moving generally and to varying extent in directions D, more particularly a direction D away from the facing retention tabs 320 or 325, to permit such insertion. The retention beads 321 are in proximity to or in contact with the top surface of the sidearm 112 to partially resist removal when said sidearm 112 is lifted upwards in direction I. The sidearm 112 may similarly be removably inserted in direction I into short retention channel 332 (not shown in this FIG. 2e), which has a cross-section structure that may be similar or identical to that of the long retention channel 333.

Figure 3A:
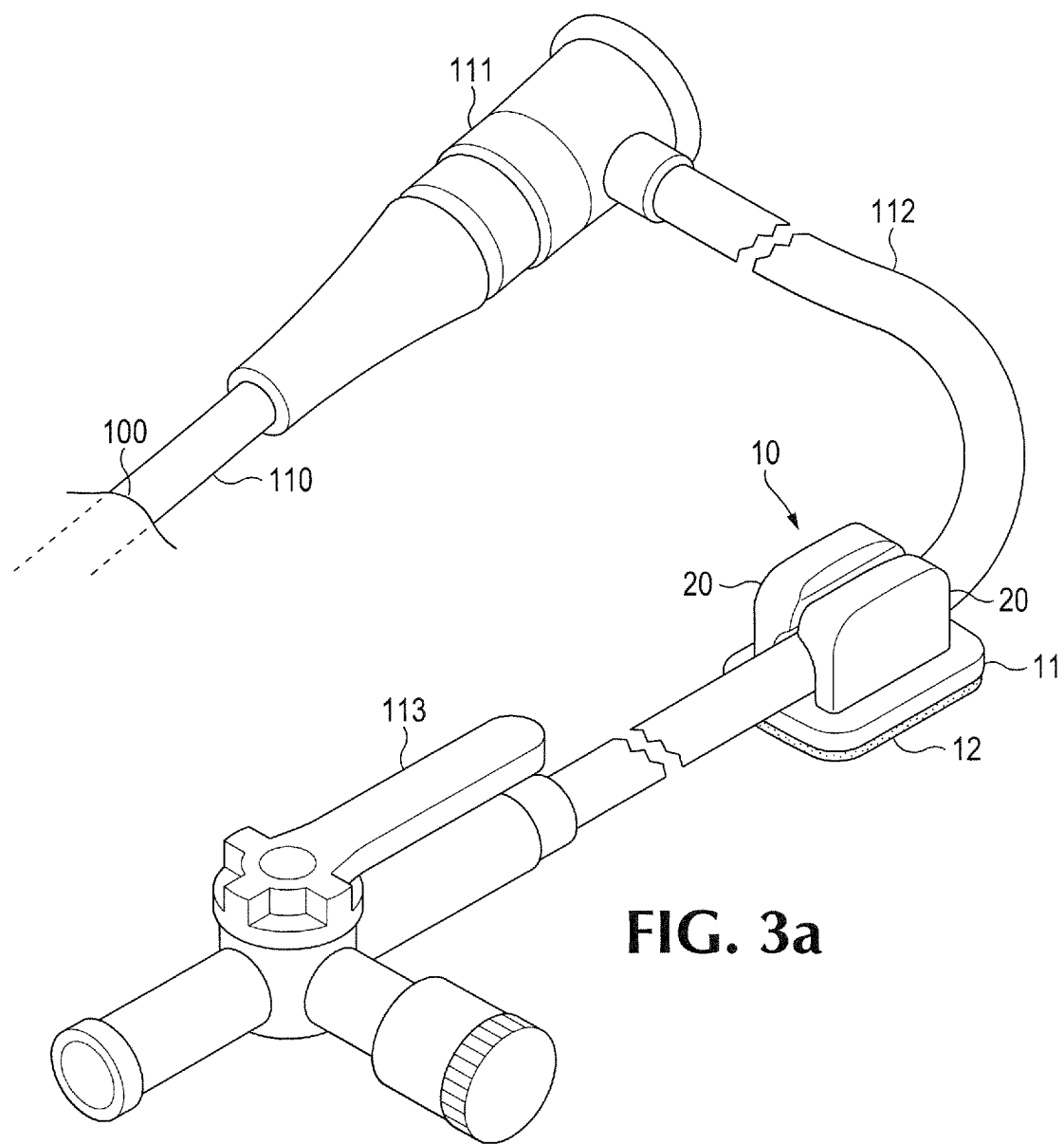
FIG. 3a is a perspective view of the sheath securement device shown in FIG. 1a in use with a vascular access sheath.

FIG. 3a shows a perspective view of the securement device 10 in use with a vascular access sheath 110 that is inserted into a puncture site 100, which is generally located in a patient's arm or wrist, but may be located near other blood vessels, e.g. a femoral artery or a dorsalis pedis artery. The sheath 110 includes a hub 111, to which is attached a flexible hollow sheath sidearm 112, at the end of which is a stopcock 113. A portion of the flexible sidearm 112 is retained between the sidearm retention tabs 20, located on the top side of securement device base 11 of the securement device 10. Adhesive 12, located on the bottom surface of base 11, adheres the device 10 to the surface upon which it is deployed, for example, a patient's skin or a drape. Alternatively, the adhesive 12 may be placed on the top surface of base 11 where a portion overlaps the perimeter of said base 11, said portion for the purpose of attaching to the surface on which it is deployed. The device 10 is shown to be positioned away from and generally to the side of the sheath 110 so as to minimize excessive exposure to blood from the puncture site 100. In this FIG. 3a, the orientation of the tabs 20 positions the sidearm 112 contained between them generally parallel to the longitudinal axis of the sheath 110.

Figure 3B:
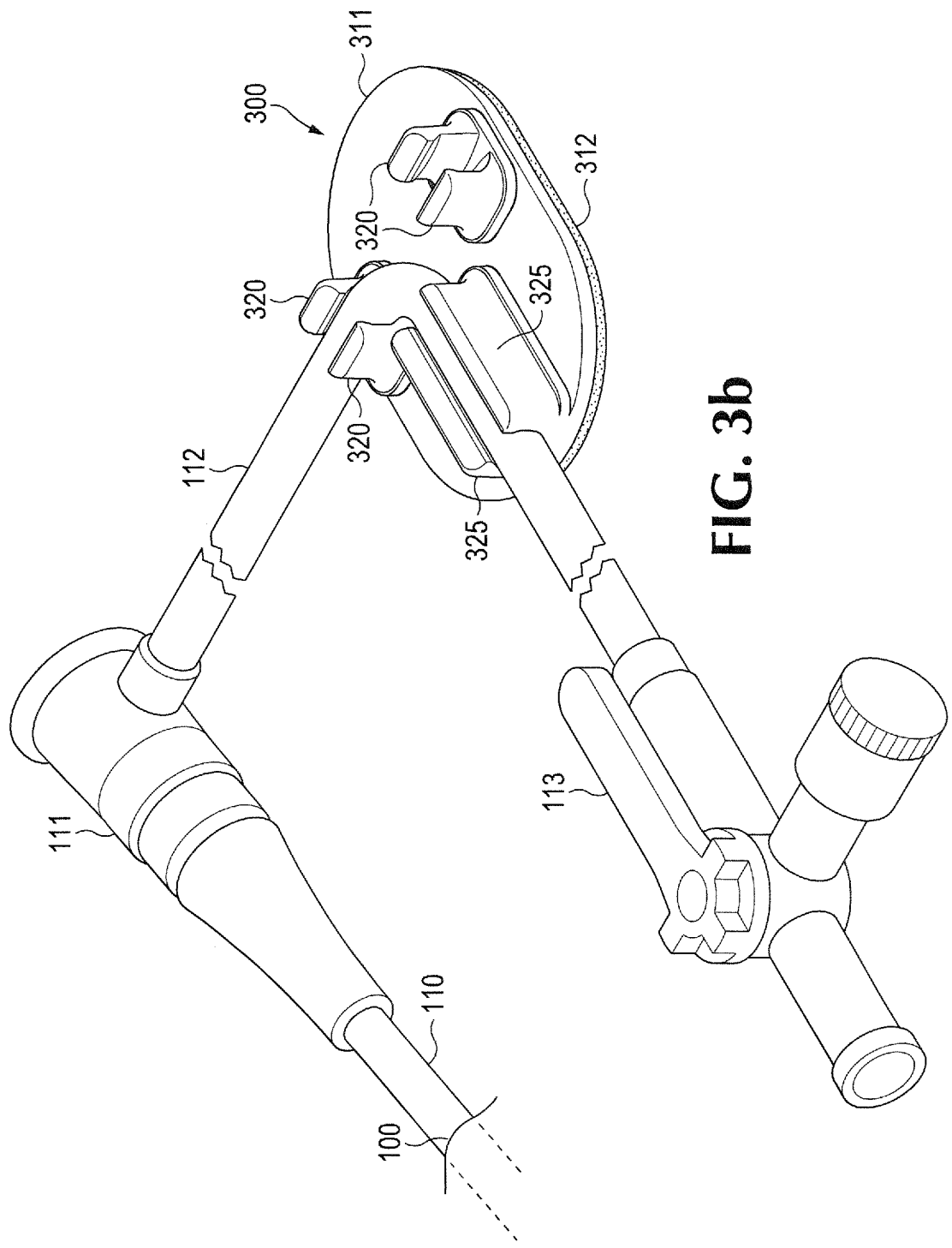
FIG. 3b is a perspective view of the sheath securement device shown in FIG. 2a in use with a vascular access sheath.

FIG. 3b shows a perspective view of the securement device 300 in use with a sheath 110 that is inserted into a puncture site 100. The sheath 110 includes a huh 111, to which is attached a flexible hollow sidearm 112, at the end of which is a stopcock 113. A portion of the flexible sidearm 112 is retained between one pair of tabs 320, located on the left edge of the top side of base 311 of the securement device 300. Adhesive 312, located on the bottom surface of base 311, adheres the device 300 to the surface upon which it is deployed, for example, a patient's skin or a drape. Alternatively, the adhesive 312 may be placed on the top surface of base 311 where a portion overlaps the perimeter of said base 311, said portion for the purpose of attaching to the surface on which device 300 is deployed. In this FIG. 3b, the orientation of the tabs 320 positions the sidearm 112 contained within generally perpendicular to the longitudinal axis of the sheath 110 and the portion of the sidearm 112 contained between retention tabs 325 parallel with the sheath 110. Notably, deployment of the device 300 is not limited to positioning of the sidearm 112 to either perpendicular to or parallel with the longitudinal axis of the sheath 110, but such positioning may be at any angle relative to the sheath 110 and the device 300 is located away from the puncture site 100 to avoid excessive exposure to blood that may issue therefrom. Clinicians experienced in radial artery vascular access will recognize that the positioning of the sheath in this FIG. 3b shows the hub 111 of the sheath positioned normally, distal to the puncture site 100, thus the stopcock 113 is shown to face proximally and the e.g., long retention tabs 325 are at the end of the device 300 that faces proximally.

Figure 4A:
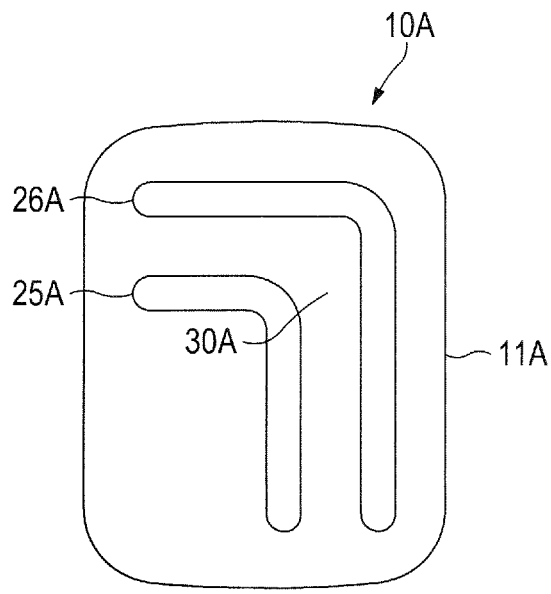
FIG. 4a shows a top view of an alternative sheath retention channel on the securement device.
Figure 4B:
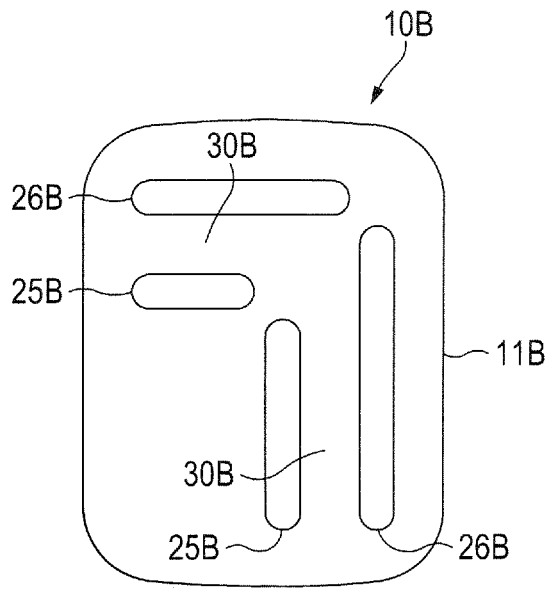
FIG. 4b shows another top view of another alternative sheath retention channel on the securement device.
Figure 4C:
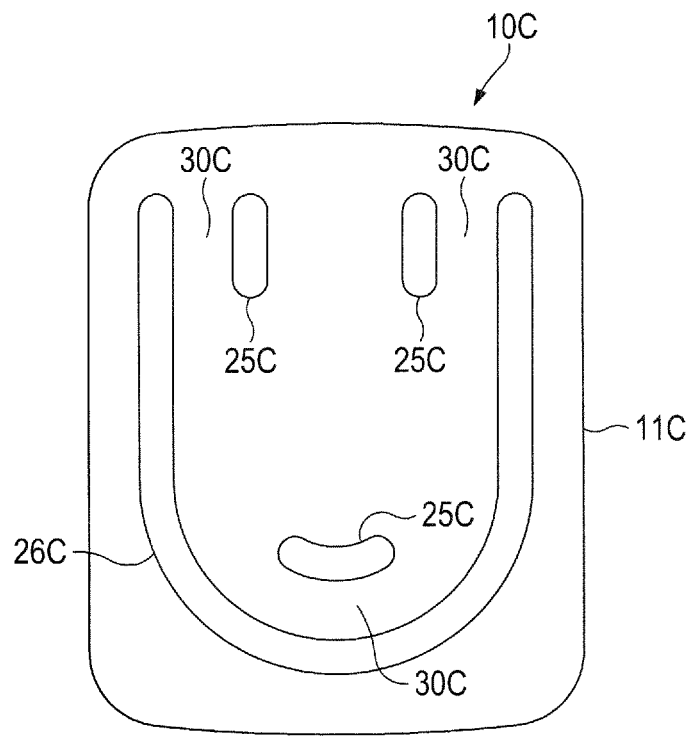
FIG. 4c shows another top view of another alternative sheath retention channel on the securement device.

FIGS. 4a through 4c are exemplar illustrations of alternative configurations of the tabs 20. Any configurations of the sidearm retention tabs 20 that serve to capture and retain the sheath sidearm 112 may similarly be considered to be within the scope of the present invention.

The top view of FIG. 4a shows a non-invasive interventional sheath securement device 10A having an inner retention tab 25A and an outer retention tab 26A that together form the sidearm retention channel 30A, all located on the top side of the base 11A. The tabs 25A and 26A and the channel 30A generally form two straight segments joined continuously at the apex of an angle, in this view, shown as a right angle, though any angle less than 180° may be suitable.

FIG. 4b shows a non-invasive interventional sheath securement device 10B having at least two inner retention tabs 25B and at least two outer retention tabs 26B that together form the sidearm retention channel 30B, all located on the top side of the base 11B. The tabs 25B and 26B and the channel 30B generally form two straight segments joined continuously at the apex of an angle, in this view shown as a right angle, though any angle would suffice. The plurality of tabs 25B and 26B affords independent flexing of each of the tabs to permit easier insertion of an object into the channel 30B when said tabs are formed of a semi-rigid or flexible material.

FIG. 4c shows a non-invasive interventional sheath securement device 10C having at least two (in this view there are three shown) inner retention tabs 25C and at least one outer retention tab 26C that together form the sidearm retention channels 30C, all located on the top side of the base 11C. The tabs 25C and 26C and the channel 30C generally form at least a first two straight segments joined continuously by at least one additional segment that runs non-parallel to the first straight segments, in this view shown generally in a U shape. The plurality of tabs 25C and 26C affords independent flexing of each of the tabs to permit easier insertion of an object, e.g. a sidearm 112, into the channel 30C.

Figure 5A:
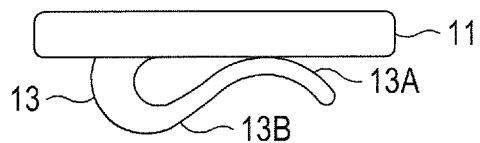
FIG. 5a shows a side view of an alternative embodiment of a means of attaching the securement device.
Figure 5B:
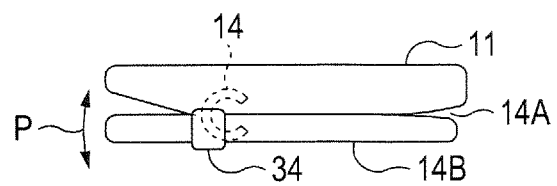
FIG. 5b shows a side view of another alternative embodiment of a means of attaching the securement device.

FIGS. 5a and 5b show clamping mechanism alternatives to using adhesive on the bottom sides of the base 11 for the purpose of attaching the non-invasive interventional sheath securement device 10, 10', 10", 10A, 10B or 10C to the drape surrounding the puncture site 100, or to an adjacent towel or fabric. The Figures show said clamping mechanisms located on the bottom side of base 11, however, it will be recognized that the same functionality may be achieved by locating them on a perimeter edge of base 11 and these configurations are within the scope of the present invention.

The side view of FIG. 5a shows a clamping mechanism that includes a securement spring 13 located on the bottom side of base 11 into which a fold of a drape or towel may be inserted through spring opening side 13A and held in place by spring arm 13B pressing against the bottom surface of base 11.

The side view of FIG. 5b shows a clamping mechanism that includes a securement c-spring 14, attached to base 11 and c-spring arm 14B, applying closing force to c-spring arm 14B that is held in place and allowed to pivotably move P by c-spring arm brackets 34 connecting it to the base 11. A fold of a drape or towel may be inserted into c-spring arm opening side 14A when said arm 14B is pressed open. When allowed to close, the c-spring arm 14B clamps the fold of a drape or towel between its top surface and the bottom surface of base 11.

Figure 6A:
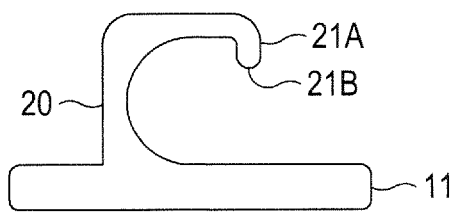
FIG. 6a shows an end view of an alternative embodiment of a retention tab.

FIG. 6a shows an end view of an embodiment that includes a single tab 20 located on the top surface of a base 11, the tab 20 having a retention bead 21A and overhang 21B. A sidearm retention channel 30 is located between the tab 20, bead 21A and overhang 21B. Tab 20 may flex when an object is inserted into the channel 30, in a fashion similar to that described in Figures previously presented in the present application. An adhesive material 12 or spring (neither shown in the FIG. 9) may also be included.

Figure 6B:
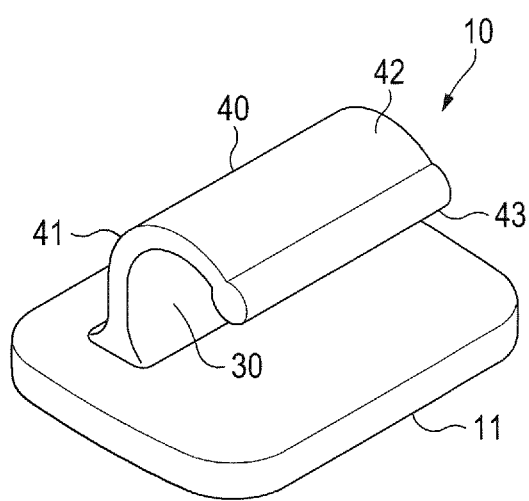
FIG. 6b shows a top perspective view of an alternative embodiment of a securement device.

FIG. 6b shows a top perspective view of an embodiment of a non-invasive interventional sheath securement device 10 that includes a base 11 on top of which is located a sidearm retention hook 40 that is comprised of at least a retention hook base 41 and a retention hook top sidewall 42 that together with the top surface of the base 11 form a sidearm retention channel 30. A retention hook ledge 43 is located at the edge of the hook top sidewall 42 opposite the hook base 41. A sidearm 112 (not shown in this FIG. 10a) is inserted into the channel 30 by pressing it under the ledge 43 and under the top sidewall 42.

In the interest of brevity of description, references to securement device 10 in the remainder of this specification shall also mean device 10', 10", 10A, 10B, and 10C. Similarly: i) references to base 11 shall also mean base 11', 11A, 11B, or 11C; ii) references to tabs 20 shall also mean tabs 20, 22, 25A, 25B, 25C, 26A, 26B, and 26C. Though each of the embodiments presented herein include slightly differing sets of features, it will be understood that such features may be exchanged from one device to the other although such combinations are not explicitly presented herein.

Although not shown in the Figures, a finger tab or thumb tab may be attached to the top ends of the tabs 20, 320 or 325, or ledge 43, for the purpose of enabling easier manipulation of the device 10, in particular during insertion and removal of the sidearm 112 into the retention channels 30, 30', 31, 332 and 333.

It can be seen that the sheath sidearm retention tabs 20, 320 and 325 function as a form of cantilevered beam or cantilevered lug in a cantilever snap-fit joint, because they are able to deflect (i.e. generally and to varying extent, flexing in direction D), and sheath sidearm retention beads 21 and 3211 are formed as a hook on the end of such cantilevered beam or lug, thus creating sheath sidearm retention channels 30, 332 and 333. The interior sides of the tops of the beads 21 and 321 have a bevel that slants inward and downward to facilitate insertion of the sidearm 112. The interior sides of the bottoms of the beads 21 and 321 have a bevel that slants upward and inward to facilitate removal of the sidearm 112. One or more beads 21 and 321 may have such bevels.

In another embodiment, a sheath sidearm retention bead 21A may extend further away from the vertical axis of the tab 20 than bead 21 and include a catchment feature, for example an extended rim or overhang 21B extending downwards at the tip of retention bead 21A towards the top surface of the base 11, that can be used to capture a sidearm 112 without the need for a second tab 20. Bead 21A and overhang 21B may similarly be present on tabs 20.

The inside surfaces of the retention tabs 20, 320 and 325 that face the retention channels 30, 332 or 333 preferably have a relatively high coefficient of friction so as to limit or prevent slidable movement of an object, for example a sidearm 112, through said channels 30, 332 or 333 when equipment is passed in and out of the hub 111 of the sheath 110, thus helping to prevent slidable movement of said sheath 110 through the puncture site 100.

The surface area covered by the securement devices 10 and 300 is between one quarter of a square inch and 10 square inches, more particularly between one square inch and five square inches. The footprint of the bases 11 and 311 may have a round, oval, square, elongate, rectangular or other shape, all of these being within the scope of the present invention. The tabs 20, 320 and 325 may have different dimensions, e.g. the length and height of one may be different from another located on the same securement device base 11 or 311. Certain embodiments may: i) dimension said tabs 20 as higher than the outside diameter of a sidearm 112, i.e. the distance from the base 11 or 311 to the top edge of said tabs 20, 320 and 325 is longer than the outside diameter of sidearm 112; ii) have lengths that are longer than their thickness, and they may also extend beyond the perimeter edge of base 11 or 311; and, iii) be positioned generally opposite each other or in line (i.e. end to end) with each other. The shapes and relative dimensions shown in the Figures are for illustrative purposes to demonstrate the features of the device 10 and 300, and their functions.

The preferred embodiment of a non-invasive interventional sheath securement device 300 includes a securement device base 311 and: i) at least one of sheath sidearm retention tabs 320 or 325, at least one of which includes a sheath sidearm retention bead 321, and ii) at least one of sheath sidearm retention channels 332 or 333. The device 300 may optionally further include at least one of an adhesive 312, located on one or both of the bottom and top surfaces of the base 311, or an attachment clamp located on the bottom or a perimeter edge of base 311. At least one of channels 332 or 333 may further have an internal taper, i.e. an interior width between the tabs 320 or 325, that varies continuously from one end to the other, more particularly a width C located in the middle of channels 332 or 333 that is smaller in dimension than a width E that is located at one of more of the channels' 332 or 333 exterior ends. The channels 332 and 333 are for the purpose of removably capturing a sheath sidearm 112 during the sheath's 110 deployment in a medical procedure by sidearm's 112 insertion in direction I into the channels 332 or 333. As shown in the Figures: i) the placement of the channels 332 and 333 are at non-parallel angles to each other, an example being shown in FIGS. 2a and 2d where channels 332 are arranged apart from and at a non-parallel angle, more particularly a 90° angle, to channel 333; ii) the channels 332 and 333 are open on one side, in particular their top sides, and at both of their ends to permit removable insertion of the sidearm 112 for simultaneous placement into the separate channels 332 and 333 as shown in FIG. 3h; and, iii) the internal taper of the channels 332 and 333 is formed by convex inside walls of the sidearm retention tabs 320 and 325, i.e. the inside walls of the sidearm retention tabs 320 and 325 that face the center of such channels 332 and 333 are convex in shape, i.e. the width C in their centers is smaller than the width E at one or both of their two ends.

An alternative embodiment of a sheath securement device 10 includes a securement device base 11 and at least one of a sheath sidearm retention channel 30 or an embedded sheath sidearm retention channel 31. At least one of a sheath sidearm retention tab 20, at least one of which may optionally further include a sheath sidearm retention bead 21, is present if the retention channel 30 is included. The securement device 10 may further include at least one of an adhesive 12 or attachment clamp located on the bottom side or a perimeter edge of base 11. At least one of channels 30 or 31 may further have an interior internally tapered width between the tabs 20, i.e. said width has a width C located in the middle of the at least one channel 30 that is smaller in dimension than a width E that is located at one or more of the exterior ends. As shown in the Figures, this internal taper of the channels 332 and 333 is formed by convex inside walls of the sidearm retention tabs 320 and 325, i.e. the inside walls of the sidearm retention tabs 320 and 325 that face the center of such channels 332 and 333 are convex in shape, thus more particularly forming convex internally tapered channels 332 and 333.

Another alternative embodiment of the sheath securement device is device 10 that includes at least a base 11, at least one retention tab 20 forming a retention channel 30, and a retention bead 21A and overhang 21B. The securement device 10 may further include at least one of an adhesive 12 or attachment clamp located on the bottom side or a perimeter edge of base 11, or overlaid on the top surface of base 11 such that it overlaps onto the surface onto which the device 10 is placed. At least one of channels 30 may further have an interior internally tapered width between the tabs 20, that varies continuously from one end to the other, more particularly a width C located in the middle of the at least one channel 30 that is smaller in dimension than a width E that is located at the exterior ends. This internal taper of the channel 30 is formed by convex inside walls of the sidearm retention tabs 20, i.e. the inside walls of the sidearm retention tabs 20 that face the center of channel 30 are convex in shape, thus more particularly forming a convex internally tapered channel 30.

Another alternative embodiment of the device 10 includes a base 11 on the top surface of which is located at least a retention hook 40 that further includes a retention hook base 41 and retention hook top sidewall 42. A retention hook ledge 43 is located at the edge of the top sidewall 42, and a channel 30 is located under it. At least one of channels 30 may further have an interior width between the tabs 20, that varies from one end to the other, more particularly a width C located in the middle of the at least one channel 30 that is smaller in dimension than a width E that is located at one or more of the exterior ends.

Adhesive material 12 may be applied on the bottom surface of the base 11 or adhesive 312 may be overlaid onto the top surface of base 311 such that a portion of it overlaps past the perimeter of bases 11 or 311 for the purpose of adhering to the surface onto which the device 300 is placed.

Certain other embodiments of the device 300 may have channels 332 or 333 embedded into the base 311, similarly to the embedded sheath sidearm retention channel 31, which may alternatively be entirely or partially embedded in base 11 of the device 10'.

Ancillary features, for example, a hook or loop or flap located on base 11 or 311 or on the adhesive 12 or 312 for the purpose of more conveniently positioning and attaching or removing the device 10 or 300 are not shown in the Figures, but by inclusion in this specification are also within the scope of this invention.

All elements of the securement device 10 and 300 must be durable enough to withstand use for the entire duration of an interventional medical procedure and must be composed of materials that can be sterilized. All or parts of adhesives the devices 10 and 300, in particular those elements included in or on the bases 11 and 311, may optionally be formed by injection molding as a single unitary element except for the adhesive materials 12 and 312. Alternatively, they may be milled or 3D-printed. The materials used may be rigid after forming, or be flexible, for example, having a Shore D durometer of approximately 50 to 85 or a Shore A durometer of approximately 70 to 95. Examples of resins that may be used include polypropylene, nylon, ABS, polystyrene, polycarbonate, copolyester, acrylic, polyurethane, rubber, polyamide, delrin, metals, composites, or silicone. The tabs 20, 320 and 325 may be formed as rigid members, or they may be formed as having the characteristic of flexibility, either at a single point along their widths or lengths, or along their entire widths or lengths. For example, the tabs 20, 320 and 325 may flex only in the area at which they are attached to the bases 11 and 311. More particularly such semi-rigid thermoplastic may permit flexing, to limited extent, i.e. from 1 degree to 10 degrees, from the vertical axis, in directions D when an object, for example a sidearm 112, is pressed down into or pulled up out of the channel 30, 332 and 333 in the vertical axis I.

The adhesive materials 12 and 312 may be of a thickness less than 0.50 inches At least a portion of the bottom surface of the adhesive materials 12 and 312 is adhered to the surfaces onto which the devices 10 and 300 are deployed.

All materials preferably are compatible with medical device sterilization techniques well known to those skilled in the art, and which include gamma ray and ethylene oxide.

The channels 30, 332 and 333 preferably have a maximum width that does not exceed the expected outside diameter of a sidearm 112, and such channel 30, 332 and 333 widths or diameters may vary in dimension along their lengths, in particular, taking the form of an internally tapered channel. In particular, a width C of said internally tapered channel, located in its center portion, is smaller in dimension than a width E, located at its ends. Width C may have a dimension of 0.07 to 0.10 inches, more particularly, less than 0.09 inches. Width E may have a dimension of 0.09 to 0.12 inches, more particularly, larger than 0.10 inches. The distance between the facing sides of the beads 21 or 32I may have dimensions of 0.06 to 0.09 inches, more particularly, less than 0.08 inches.

The channels 30, 332 and 333 are all open at their ends and continuously along the entire length of at least one side. In all embodiments except that shown in FIGS. 6a and 6b, the channels 30, 332 and 333 are open along the entire length of their top-facing sides, i.e. on the sides directly opposite the bases 11 and 311. This enables a sidearm 112 to be conveniently inserted into the devices 10 and 300.

A method of use for a preferred embodiment of device 300 generally includes the following steps, in sequence: i) a protective liner on the underside of the adhesive 312 is removed; ii) the device 300 is adhered onto a patient's skin or onto a drape near the puncture site 100, preferably proximal to, and either medial or lateral to, said puncture site 100, with the exterior end of the long channel 333 facing the patient's elbow as shown in FIG. 3b; iii) the sheath sidearm 112 is pushed into a first short channel 332, i.e. facing the puncture site 100, and then into the long channel 333 or, alternatively, the sidearm 112 may be inserted into the short second short channel 332 opposite the first short channel 332. The sidearm 112 is seated under the retention beads 321 to help prevent removal of the sidearm 112 by an upward pulling motion in direction I as shown in FIG. 3e, and compression placed on the outside surfaces of the sidearm 112 prevent its slideable movement through the channels 332 and 333.

Further, when the device 300 is placed proximal to the puncture site 100 and the hub 111, as described in this method, slidable movement of said sidearm 112 is inhibited, in particular, due to the angle, approaching or at 90 degrees, of the portion of the sidearm 112 outside the first short channel 332 (i.e. closest to the huh 111) and its portion contained within the first short channel 332: the sidearm 112 does not slide past the corner of the first short channel 332 due to its retention in said channel 332 and friction against the corner. By thusly inhibiting such slidable movement of the sidearm 112 out of the first channel 332, slidable movement of the sheath 110 through the puncture site is inhibited.

The devices 10 and 300 do not rely on adhesive directly applied to any part of the sheath 110 or sidearm 112 for securement, nor do they have hinges or other moving parts for sheath 110 or sidearm 112 capture or retention.

It will be understood that the present invention is not limited to the method or detail of construction, fabrication, material, application or use described and illustrated herein. Indeed, any suitable variation of fabrication, use, or application is contemplated as an alternative embodiment, and thus is within the spirit and scope of the present invention. Similarly, features shown or described herein may be combined in ways not explicitly mentioned or illustrated, however these are within the scope of the present invention. For example: i) a single internally tapered channel 332 formed between two tabs 320 may be included on a frame 311 together with a two channels 333 formed between two pairs of tabs 325, one of which includes a bead 321, together with adhesive 312 that is attached to the base's 311 bottom surface: ii) the device 300 may be supplied without adhesive 312 attached to it, in particular if the user provides an adhesive material for deployment, or if a mechanical clamping means is included, such as are shown in FIGS. 5a and 5b; iii) an embedded channel 31 having an internally tapered width, open ends and an open top side may be included in base 311, with no retention tabs 20, 22, 320 or 325 present, and adhesive 312 placed over the top surface of said base 311, said channel 31 having a generally circular cross section that is truncated on its top side; iv) the device 300 may include one retention channel 333, the retention tabs 325 forming it having convex inside walls, and another retention channel 332 the retention tabs 320 forming it having straight, i.e. non-convex inside walls, said channel 332 is of constant width from end to the other.

It is further intended that any other embodiments of the present invention that result from any changes in application or method of use or operation, configuration, method of manufacture, shape, size, or material, which are not specified within the detailed written description or illustrations contained herein yet would be understood by one skilled in the art, are within the scope of the present invention.

Accordingly, while the present invention has been shown and described with reference to the foregoing embodiments of the invented apparatus, it will be apparent to those skilled in the art that other changes in form and detail may be made therein without departing from the spirit and scope of the invention as defined in the appended claims.

We claim:

1. A non-invasive interventional sheath securement device, which includes at least a sheath securement device base on a top surface of which are separately located two or more pairs of sheath sidearm retention tabs that face each other, each of the two or more pairs of sheath sidearm retention tabs forming at least one sheath sidearm retention channel between their inside surfaces, wherein:
at least two sheath sidearm retention channels are separately located on the top surface of said securement device base;
each of the sheath sidearm retention channels are open on at least one side and on both of two ends;
each of the sheath sidearm retention channels is configured to engage a single, flexible sheath sidearm when said sheath sidearm is removably inserted therein through one of its at least one open sides;
at least one sheath sidearm retention channel is placed on the top surface of said sheath securement device base apart from and at a non-parallel angle to at least one of the other said sheath sidearm retention channels so as to enable the simultaneous capture in both of at least two retention channels of the sheath sidearm inserted therein at different locations along said sidearm's length.

2. The sheath securement device of claim 1 that further includes at least one of: a clamping mechanism located on a bottom surface or a perimeter edge of said base; an adhesive material located on a top side of said base that further overlaps beyond the perimeter edge of said base.

3. The sheath securement device of claim 1 wherein at least one of the sheath sidearm retention channels comprises an internally tapered sheath sidearm retention channel having a center and two open ends, the center and two open ends having widths, wherein the width at the center is smaller than the width at both of its two ends.

4. The sheath securement device of claim 1 wherein at least one of the sheath sidearm retention tabs in the two or more of the pairs of sheath sidearm retention tabs further includes a sheath sidearm retention bead located on at least a part of a length of an inside surface of a top portion of said retention tabs.

5. The sheath securement device of claim 1 wherein the two or more pair of sheath sidearm retention tabs comprise: i) at least one pair of short sheath sidearm retention tabs that form at least one short sheath sidearm retention channel, and, ii) at least one pair of long sheath sidearm retention tabs that form at least one long sheath sidearm retention channel.

6. The sheath securement device of claim 1 wherein at least one of the sheath sidearm retention tabs in the two or more of the pairs of sheath sidearm retention tabs that form a sheath sidearm retention channel flexes at least in a direction away from the facing sheath sidearm retention tab when a sheath sidearm is inserted into said sheath sidearm retention channel through its open side, to permit insertion and removal of the sheath sidearm.

7. The sheath securement device of claim 1 wherein the sheath sidearm, when inserted into the at least two retention channels, has a segment of its length, located between the portions retained in the at least two retention channels, that has a curve at an angle that is generally the same as the non-parallel angle of relative placement of said at least two retention channels, thereby inhibiting said sidearm's slidable movement therethrough.

8. The sheath securement device of claim 1 that further includes at least an adhesive material located on a bottom side of the base of said device base.

9. A non-invasive interventional sheath securement device that includes a sheath securement device base on a top surface of which are located two or more embedded sheath sidearm retention channel wherein:
each of said two or more embedded sidearm retention channels has a generally circular cross section that is truncated on its top side, which is open, and two ends, both of which are open;
a sidearm retention bead is placed along at least part of the edge on a top side opening of said two or more embedded sidearm retention channels;
said two or more embedded sidearm retention channels are located in the top surface of said sheath securement device base apart from and at a non-parallel angle to at least one of the other said two or more embedded sidearm retention channels so as to enable simultaneous capture of a single sheath sidearm inserted therein at different locations along its length.

10. The sheath securement device of claim 9 that further includes at least one of: an adhesive located on a bottom side of the securement device base; a clamping mechanism located on a bottom surface or a perimeter edge of said base; an adhesive material located on a top side of said base that further extends beyond the perimeter edge of said base.

11. The sheath securement device of claim 9 wherein at least one of the two or more embedded sheath sidearm retention channels comprises an internally tapered embedded sheath sidearm retention channel having a center and two ends, wherein the center has a width that is smaller than a width at both of its two ends.

12. The sheath securement device of claim 9 wherein the two or more embedded sidearm retention channels comprise: i) at least one short embedded sidearm retention channel, and, ii) at least one long embedded sidearm retention channel.

13. The sheath securement device of claim 9 wherein the sheath sidearm, when inserted into the two or more embedded sidearm retention channels, has a segment of its length, located between the portions retained in said embedded sidearm retention channels, that has a curve at an angle that is generally the same as the non-parallel angle of relative placement of said embedded sidearm retention channels, thereby inhibiting said sidearm's slidable movement therethrough.

14. An internally tapered sheath sidearm retention channel, located on a top surface of a non-invasive interventional sheath securement device, said internally tapered retention channel being configured to removably receive a sheath sidearm, wherein:
said internally tapered retention channel has two ends, which are both open, and is formed between internal surfaces of two sheath sidearm retention tabs, said internal surfaces facing each other;

a top side of said internally tapered retention channel is open to permit the sheath sidearm to be removably inserted therein;

said internally tapered retention channel has a width at its center and widths at its ends wherein the width at the center is smaller than the widths at both ends;

one or more of said retention tabs includes a sheath sidearm retention bead located on at least part of a length of an inside surface of a top portion of said retention tabs.

15. The internally tapered sheath sidearm retention channel of claim 14 wherein at least one of the sheath sidearm retention tabs is configured to flex in a direction away from the facing sheath sidearm retention tab when a sheath sidearm is inserted into said internally tapered sheath sidearm retention channel through its open top side.

* * * * *